(12) United States Patent
Nablo et al.

(10) Patent No.: US 6,221,216 B1
(45) Date of Patent: Apr. 24, 2001

(54) TECHNIQUE FOR INTERIOR ELECTRON STERILIZATION OF AN OPEN MOUTHED CONTAINER

(75) Inventors: Samuel V. Nablo, Acton; Denise A. Cleghorn, Dracut, both of MA (US)

(73) Assignee: Electron Processing Systems, Inc., N. Billerica, MA (US)

( * ) Notice: Subject to any disclaimer, the term of this patent is extended or adjusted under 35 U.S.C. 154(b) by 0 days.

(21) Appl. No.: 09/380,343

(22) PCT Filed: Mar. 25, 1998

(86) PCT No.: PCT/US98/05755

§ 371 Date: Aug. 30, 1999

§ 102(e) Date: Aug. 30, 1999

(87) PCT Pub. No.: WO98/42385

PCT Pub. Date: Oct. 1, 1998

Related U.S. Application Data (60) Provisional application No. 60/041,704, filed on Mar. 26, 1997.

(51) Int. Cl.[7] ............................................ C07C 7/00
(52) U.S. Cl. ............................... 204/157.15; 422/186.06
(58) Field of Search ....................... 204/157.15, 158.2, 204/198; 422/186, 186.05, 186.06

(56) References Cited

U.S. PATENT DOCUMENTS

| | | | |
|---|---|---|---|
| 3,780,308 | * 12/1973 | Nablo | 250/492.3 |
| 4,345,545 | 8/1982 | Miller | 118/621 |
| 4,652,763 | * 3/1987 | Nablo | 250/492.3 |
| 4,666,678 | 5/1987 | Lemelson | 422/186 |
| 5,635,714 | * 6/1997 | Nablo | 250/305 |

* cited by examiner

*Primary Examiner*—Kathryn Gorgos
*Assistant Examiner*—Thao Tran
(74) *Attorney, Agent, or Firm*—Neilds & Lemack (57) ABSTRACT

Commercial sterilization of the interior surfaces of containers, cups or bottles by the use of energetic electrons is accomplished by directing electrons of moderate energies through the open mouth of such containers. Electrons which would normally illuminate the container beyond the inner diameter of the neck opening may be absorbed by a suitable electron-absorbing and cooled mask positioned above the container neck.

16 Claims, 7 Drawing Sheets

TECHNIQUE FOR INTERIOR ELECTRON STERILIZATION OF AN OPEN MOUTHED CONTAINER

This application claims the benefit of provisional application Ser. No. 60/041,704, filed Mar. 26, 1997. This application is a 371 of PCT/US 98/05755, filed Mar. 25, 1998.

BACKGROUND OF THE INVENTION

1. Field of the Invention

The invention relates to electron processing, and in particular to the sterilization of containers by energetic electrons.

2. Description of the Related Art

There are many applications of container sterilization (both for medical, pharmaceutical and food packaging) where the low temperatures involved with electron treatment are desirable. For example, for glass containers, superheated steam, flame or infra-red are used at temperatures from 275°–400° C. Such temperatures pose serious problems due to thermal shock. For example, using the Dole process, and non-pressurized superheated steam, the glass is elevated to 216° C. and exits the sterilizer at an elevated temperature because of the high thermal capacity of the glass. It was found necessary to reduce the container temperature to a differential of 33° C. between the container temperature at the point of fill and the cold sterile product. The speed and cost of heat removal makes such a process unacceptable for commercial use (see Von Bockelmann, B., Ch. 48, p. 841, "Aseptic Packaging"; "Disinfection, Sterilization and Preservation", ed: S. B. Block, Lea and Febiger, Phila Pa. (1991)).

For polymer containers made of blow molded plastics such as polyester or polypropylene, hydrogen peroxide in combination with heat or with high intensity ultraviolet irradiation, is usually employed.

Figure 1:
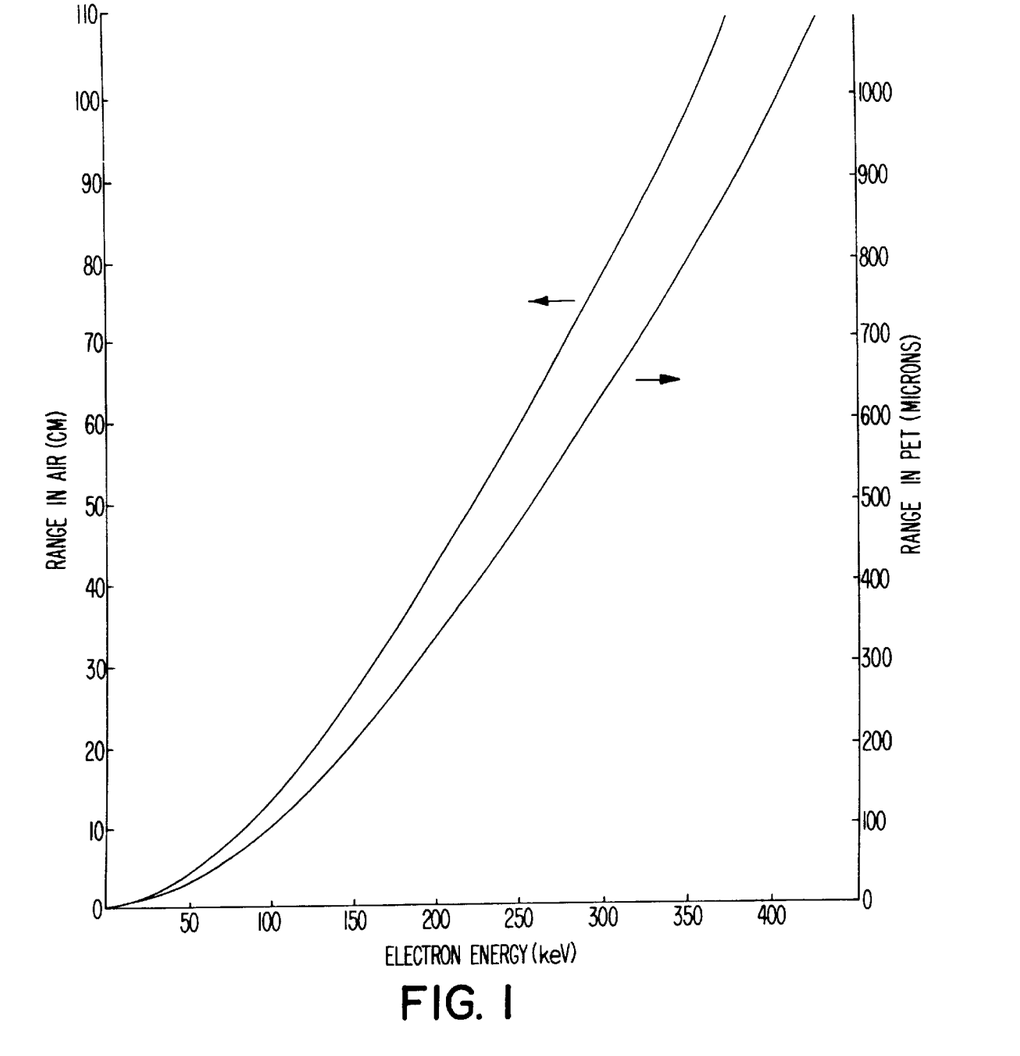
FIG. 1 is a graph showing electron penetration capability in air and polyethylene terephthalate.

The use of energetic electrons for the commercial sterilization of containers, such as those used for sterile product packaging in the pharmaceuticals and food industries, has been severely limited because of the inability of electrons of moderate energies (e.g. 100–300 keV) to penetrate the walls of the glass and blow-molded polymer containers typically used. The lower curve of FIG. 1 shows the end point of penetration or extrapolated ranges of electrons of varying energies in polyester ($\rho=1.40$ g/cc). With unilateral irradiation, the electrons, once having penetrated the side walls, must be capable of reaching all regions of the container's interior, which may then involve air paths of 10–20 cm. The penetration in air at normal temperature (see Berger, M. J. and Seltzer, S. M., "Stopping Powers and Ranges of Electrons", NBSIR-82-2550 (1983), and pressure is shown in the upper curve of FIG. 1. Hence for typical polymer containers with wall thicknesses of 500–700 microns and practical diameters, electron energies well above 300 keV would be required for "through the wall" sterilization. Such energy sources are no longer easy to radiation shield for convenient, in-line use due to the penetrating bremsstrahlung generated at the higher energies (see Radiation Shielding, ed. J. K. Shultis and R. E. Faw, Prentice Hall PTR, Upper Saddle River, N.J. 07458 (1996)).

The term "electron opaque" is used in this teaching to describe container wall thicknesses which are at least 60% of the electron's extrapolated range in that material.

Based upon a knowledge of the depth:dose curves for energetic electrons, that is, the manner in which they deliver dose to matter as they near their range end points, one selects an energy for these applications for which the electron possesses an end point or range ~1.6 times that required. For example, referring to FIG. 1, a typical 300 ml glass juice bottle has a depth of 14 cm. and a diameter of 6.5 cm. Hence a beam energy of 150 keV or more would be selected. For a 2000 ml polyester juice container with a depth of 25 cm and a diameter of 11 cm, a beam energy of 200 keV or more would be required.

SUMMARY OF THE INVENTION

This invention comprehends a technique for high speed, in-line electron sterilization of the interior surfaces of open-mouthed containers, cups or bottles, where the sterilizing energy is directed through the open mouth of the vessel.

BRIEF DESCRIPTION OF THE DRAWINGS

This invention may best be understood from the following detailed description thereof, having reference to the accompanying drawings, in which

FIGS. 4(A–C) are a series of sketches showing certain bottle:window:baffle orientations.

DESCRIPTION OF THE PREFERRED EMBODIMENTS

This invention comprehends a technique for high speed, in-line electron sterilization of the interior surfaces of empty open-mouthed containers, cups or bottles, where the sterilizing energy is directed through the open mouth of the vessel. Most blow-molded or preformed containers possess wall thicknesses of 400–500 gsm (grams per square meter usually abbreviated g.m$^{-2}$); or more so that electron energies of 350 keV or more are required for wall penetration and interior treatment with unilateral irradiation. This invention comprehends an attractive alternative: namely, treatment through the opening. This invention also comprehends solution of the problem of excessively high surface doses in the mouth region if acceptable treatment levels are to be realized in the bottom inner surface of the container. Related work has been published using low energy electrons in containers offering ratios of total interior surface area (Aw) to admitting aperture or mouth area (Am) under 18 (i.e. relatively large mouth areas). (see Nablo, S. V. and Cleghorn, D. A., "Dose Distributions for Containers Electron Sterilized at Energies from 150–250 kev", Radiat., Phys. Chem. 42, #4–6, 827–831, (1993). However, that related work did not include evaluation of such a technique (i.e. high level irradiation of the mouth:neck region with low energy electrons in order to sterilize the interior and upper exterior surfaces of the container) with containers offering an unfavorable ratio of interior surface area to mouth opening area (i.e. more than 18). Clearly, in order to "illuminate" the interior surfaces with a sterilizing fluence of energetic electrons, the dose delivered to the mouth area must be "at least" the acceptable surface treatment level times x, where x is the ratio of interior surface:mouth opening area.

For a typical 2 liter container, with an opening diameter of 35 mm, the interior:mouth area ratio is ~60. Hence, if 10 kGy (1 Mrad) was accepted as a minimum internal surface treatment, at least 600 kGy (60 Mrads) would be delivered through the necked opening of the container.

The delivery of such high doses to polymeric materials would normally be of concern as melt deformation is a "threat". At 60 Megarads, for example, the specific energy absorption is 60×2.4=144 cal/g. For most polymeric materials with a specific heat of 0.5 cal/g/° C., this would suggest temperature elevations of 2–300° C., certainly well above the melt temperatures of most commercial polymers. However, for energy delivered in the form of low energy electrons, the penetration depth represents a heating of only a small fraction of the total polymer mass, so that conductive cooling of the surface heated areas dramatically reduces the bulk temperature. For example, for the necks of typical polyethylene terephthalate containers, the wall thickness is of the order of 2 mm or 2000 g.m$^{-2}$, so that 200 keV electrons penetrating less than 200 g.m$^{-2}$ into the walls are affecting less than 10% of the polymer mass.

In certain experiments conducted by us, the tolerance of this pet (polyester) for high doses of low energy electrons was evaluated, using a sterilizer at 190 kV and treating top surface sections of the container to very high doses (e.g. 1000 kGy) or an equivalent surface treatment of 240 cal/g. Internal film dosimetry on the upper inner surfaces of the bottle was also conducted to evaluate the practicability of achieving adequate dose levels (e.g. a 6D level of 10 kGy) in these "shadowed" regions while delivering acceptable doses to the opening lip and internal peripheral surfaces.

These studies revealed no major problems for the use of very high level electron treatment of this polymer, at least over the treatment times (~5 seconds) used in the trials. These times are longer than those anticipated for an in-line sterilizer running at 200/minute and above, where exposure times of the order of one second are typical.

Further experiments were conducted in a study of a large volume container with a very large area ratio: i.e., 82. These studies have established the efficacy of the process for both disinfection and sterilization of open mouthed glass, metal and polymer containers.

A collateral application of this art is the sterilization of the neck:capping surface of a filled container. For example, polymer or glass bottles which may have been sterilized with heat or chemicals such as H$_2$O$_2$ before filling or by the hot fluid during fill, may require terminal sanitizing/sterilization before capping (see von Bockelmann, B., "Aseptic Packaging", CH. 48, *Disinfection, Sterilization and Preservation,* 4th edition, ed. Seymour S. Block, Lea and Febiger, Philadelphia, (1991)). In this application the low energy, e.g. 100 kev, electrons illuminate the neck interior, neck surfaces and product surface. In a typical application, the electrons would affect less than 0.01% of the liquid in the container.

This invention also comprehends the use of an electron absorbing, and cooled, mask positioned above the bottle neck to absorb electrons which would normally illuminate the container beyond the inner diameter of the neck opening. Such a stopping aperture, as shown in FIGS. 2(A), 2(B) and 2(C), can consist of a totally stopping cooled plate, typically of a low Z material such as Aluminum to reduce backscatter, or a partially stopping absorber such as a drilled plate, so that sufficient electron transmission occurs to treat (sterilize) the exterior surface of the container.

Figure 2A:
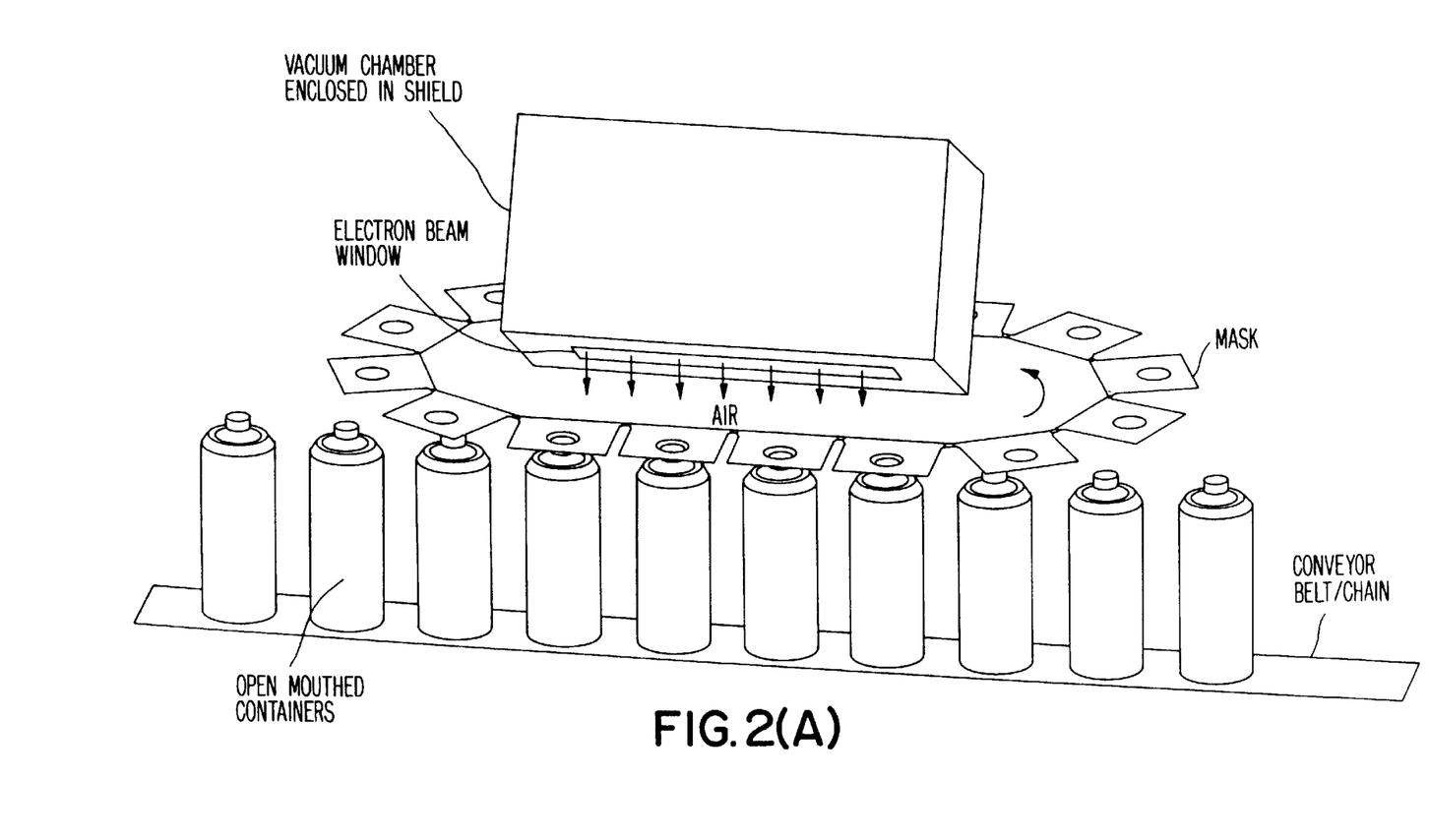
FIG. 2(A) is an isometric view of open-mouth container sterilization.

In FIG. 2(A), the electron head is tilted for clarity. FIGS. 2(B) and 2(C) are self-explanatory. The split design of FIG. 2(C) is a simpler approach as it doesn't require "insertion" of the bottle into the protective shield and simplifies container:shield indexing.

Using this masking-plate "shield", bottles of any material may be sterilized effectively at room temperature by passing them rapidly along the axis of longitudinal symmetry of a curtain type beam.

Figure 2B:
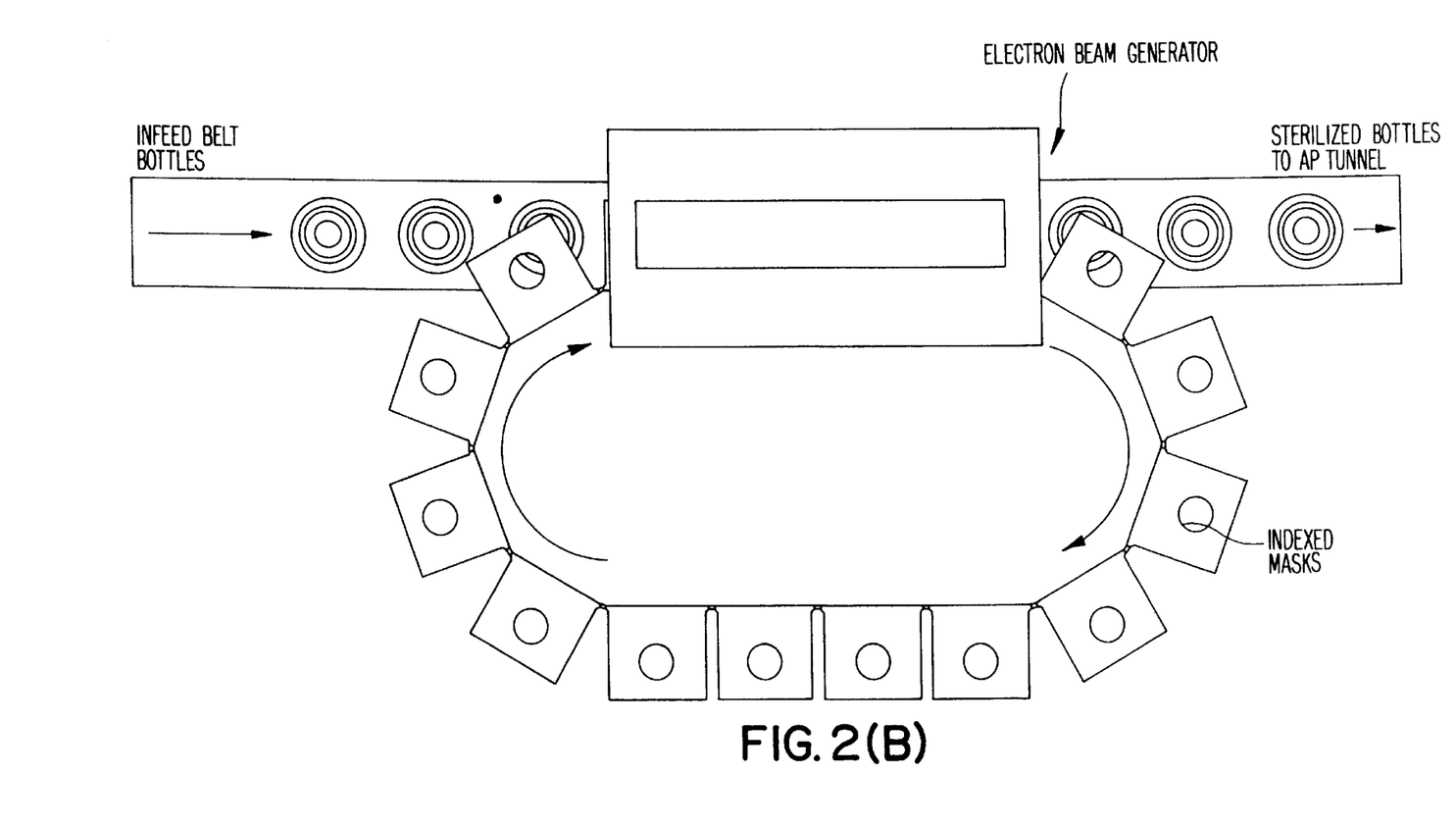
FIG. 2(B) is a schematic of electron stopping ring for open-mouth container sterilization. (Plan view)
Figure 2C:
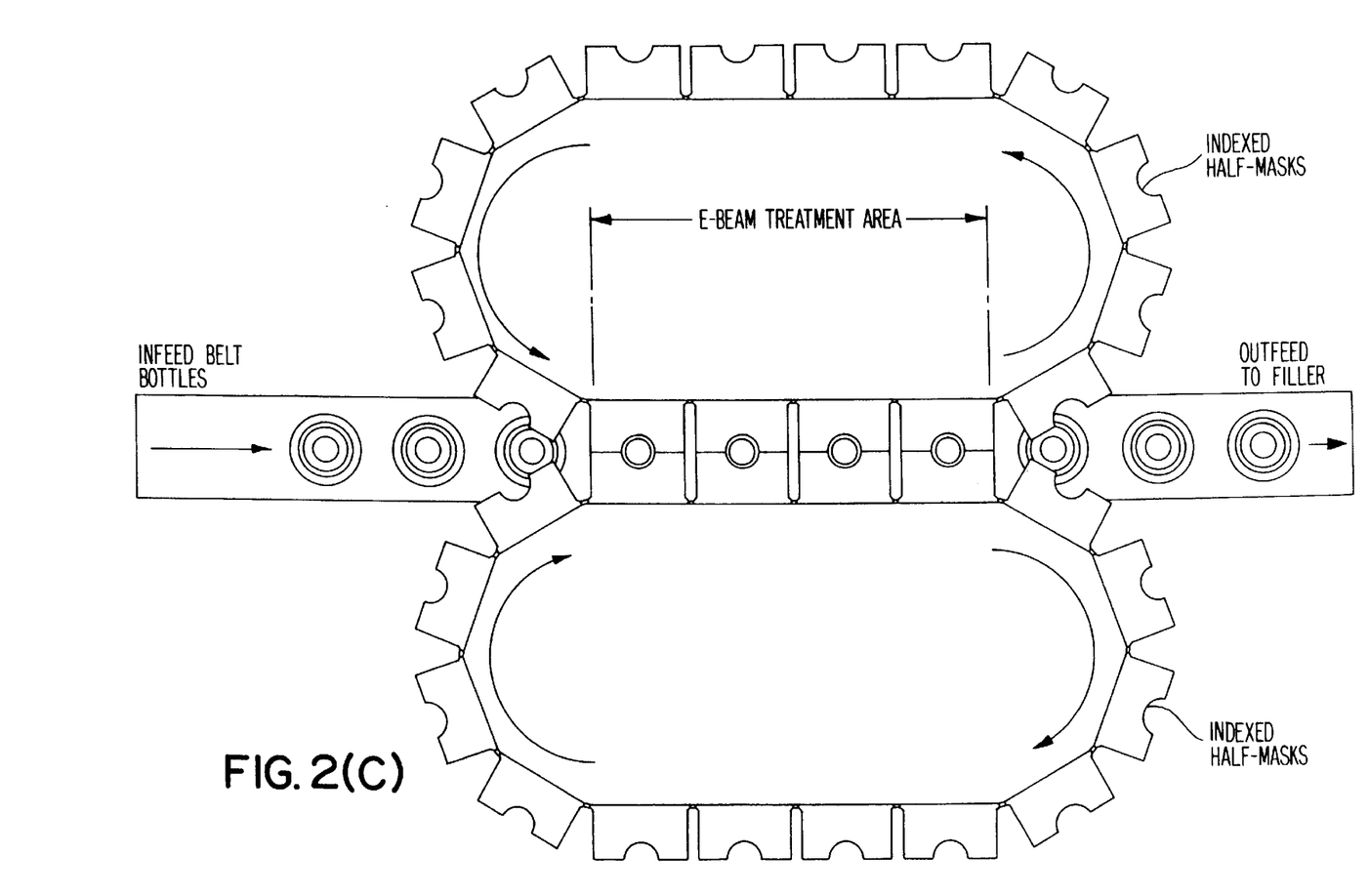
FIG. 2(C) is a plan view of a bifurcated electron stopping mask transport rings for open-mouth container sterilization.

Some simple calculations of he role of this stopping aperture as shown in FIGS. 2(A), 2(B) and 2(C), are appropriate. Suppose we need to sterilize a 2 liter blow-molded bottle whose inner surface area is ~700 cm$^2$. The open mouth of the container has a diameter of 3.5 cm or an area of ~10 cm$^2$. Using a figure of charge fluence of 1 μcoul/cm$^2$ per Megarad at the energies of interest, for example 200 kev, we would need to deliver 700 μcoul through the mouth area to suitably treat the interior surfaces. This means a fluence of 700 μcoul/10 cm$^2$ or 70 μcoul/cm$^2$ or some 70 Megarads over the container lip about the periphery of the opening. With typical specific hears of 0.5 cal/g/° C. for these polymers, the 70 Megarads (or 70×2.4= 168.0 cal/g) would elevate the polymer surface to 168÷0.5= 336° C. or well above its thermal distortion/melting point. Hence the need for the protective device described here.

Figure 3:
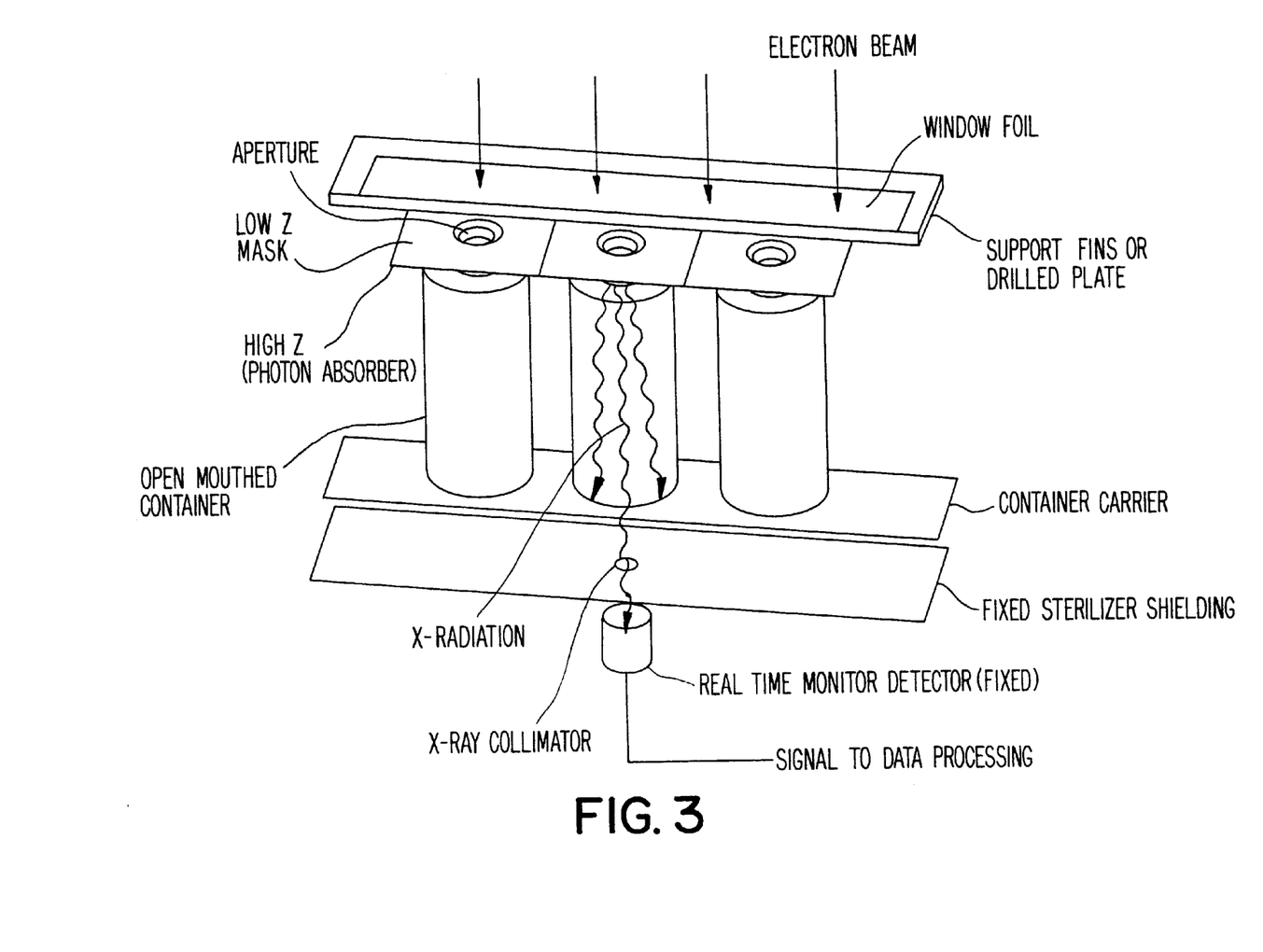
FIG. 3 is a sketch showing geometry for real time monitoring of dose rate.

This could be constructed as a recessed opening in the masking plate into which the bottle neck is inserted with appropriately designed open areas about the aperture's periphery to provide suitable illumination of the upper exterior surface of the container. Such a continuous sterilizer geometry which incorporates a real time monitor for measuring treatment dose and determining the sterility assurance level (SAL) of the process is shown schematically in FIG. 3 (see Nablo, S. V., Kneeland, D. R. and McLaughlin, W. L., "Real Time Monitoring of Electron Processors", Radiat. Phys. Chem. 46, 1337–1383 (1995).

The invention includes the following features:

1. the interior and upper exterior surface electron sterilization of an electron opaque open mouthed container by simultaneous delivery of energetic electrons to the interior surfaces through the open mouth while controlling the external surface illumination by energetic electrons from the same source. Electron energies in the range of 125 keV to 300 keV are typically used for consumer product and pharmaceutical containers in the 0.1 to 2.0 liter range.

2. the interior and upper exterior electron sterilization of an electron opaque open mouthed container already filled (completely or partially) in order to sanitize or sterilize before entrance to the capping station in the filling line.

3. an electron absorbing protective ring, suitably cooled, to prevent over dosage and thermal distortion of the capping or sealing surface of an open container's mouth.

4. spacing of the protective mask or ring from the container opening to provide adequate electron illumination of the outer surface of the container.

5. use of low Z materials in the mask to reduce electron albedo or backscatter which could affect the primary window of the sterilizer.

6. positioning of the mask on a moving assembly so that the containers may be continuously positioned under the mask and removed from it after sterilization.

7. positioning of the mask on a moving assembly which will automatically shadow the container while in the electron treatment zone but which is then removed for return to the load point after sterilization for continuous processing.

8. positioning of the mask on an assembly which moves the container linearly along the beam and returns it to its starting location before removal. In this way, a double longitudinal stroke results which will reduce the required length of the beam to accomplish the desired throughput.

9. use of a high Z photon absorber to support the low Z electron stopping plate so that a collimated stream of bremsstrahlung results as the container and aperture pass along the beam. This bremsstrahlung stream can be used with a fixed location real-time radiation monitor to verify the dose rate (electron flux) and beam energy delivered by the sterilizer (see FIG. 3) to each container, from which the actual delivered dose can be calculated and logged from the known conveyor velocity.

EXPERIMENTAL VERIFICATION AND ANALYTICAL MODELING

Using a 2 liter capacity blow molded polyester bottle, detailed studies have been conducted of the interior dose distribution delivered by electrons delivered through the mouth at varying (sterilizer) energies. For this container with a mouth diameter of 35 mm, a major interior diameter of 10 mm and a height of 270 mm, it is important that the electron energy is sufficient to transport scattered electrons through a 27 cm air path. At NTP air weighs some 12 g.m$^{-2}$ per cm of thickness so that the required penetration range is 325 g.m$^{-2}$ or greater. Since this is about the 50% dose penetration figure for electron processor operation at 225 kV, dose mapping was performed around this operating point. A protective mask with a 35 mm diameter opening was used with a thickness of 0.2 cm (5400 g.m$^{-2}$) for neck/shoulder protection of the container.

Figure 4A:
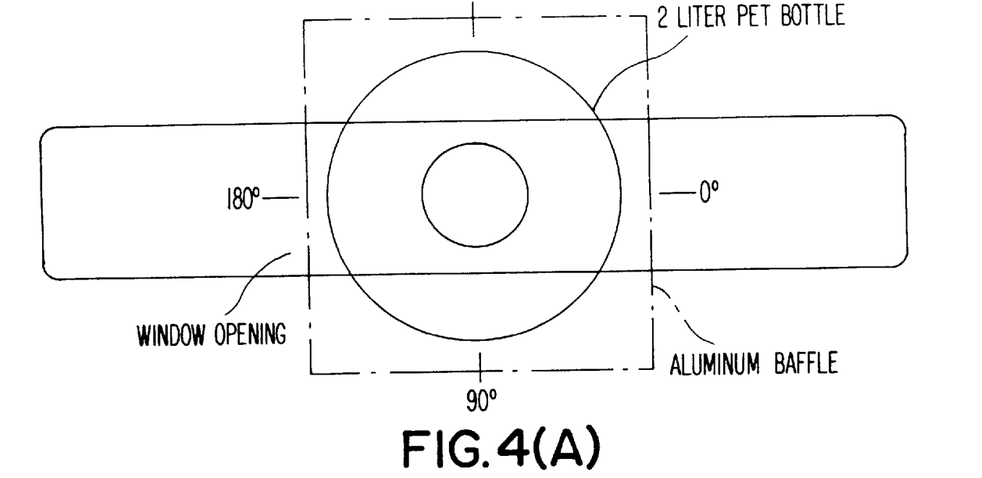
Figure 4B:
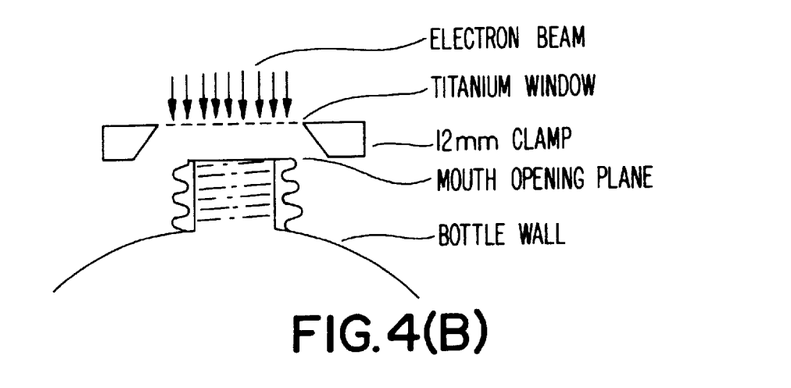
Figure 4C:
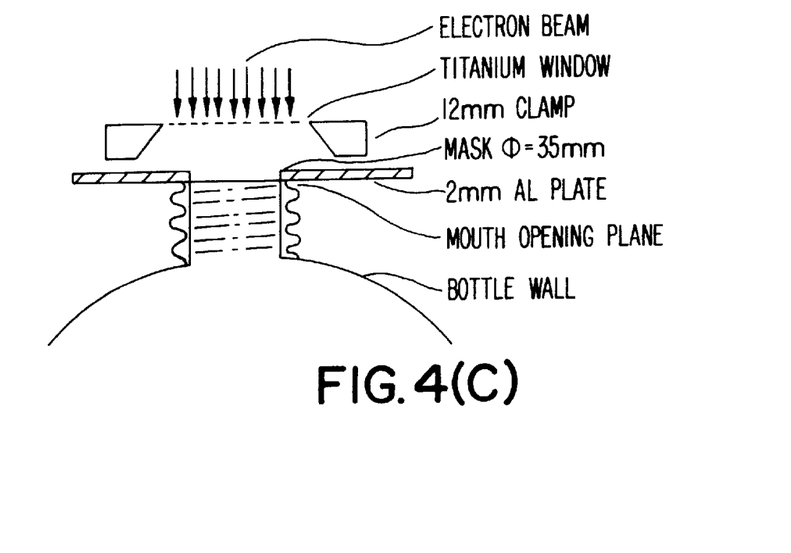

Interior surface dosimetry was conducted with 10 g.m$^{-2}$ thick FWT-810 (Far West Technology, Goleta, Calif.) radiochromic film dosimetry, with film arrayed at the 0° and 90° locations in the container, here 0° represents the longitudinal symmetry axis of the strip electron beam as showing in the orientation sketches of FIG. 4.

External or exterior surface dosimetry was conducted in the same manner, only in this case the gap between the protective mask and the bottle mouth plane could be varied to adjust the exterior surface dose levels. Detailed interior dose measurements can be conducted with film dosimetry positioned on the desired surfaces of these split containers . . . for example on 72° sectors about the bottom surface.

In order to analytically check these results, the TIGER Monte Carlo code was used for simulation of the experiment (Halbleib, J. A., Kensek, P. P., Melhorn, T. A., Valdez, D G. D., Seltzer, S. and Berger, M. J., ITS version 3.0: The Integrated TIGER Series of Coupled Electron/Photon Monte Carlo Transport Codes, SAN 91-1634, NTIS, USDOC, 525 Port Royal Road, Springfield, Va. 2216).

In order to reproduce the beam entrance conditions to the container, measurements were made of the dose distribution at the window plane and a plane m mm from the Titanium window foil. These were then compared with the modeled dose distributions developed by the code, with good agreement at the 240 kV operating voltage used in the experimental work.

In conducting the electron transport calculations, the contoured and necked bottle was approximated by a simple cylinder:cone:cylinder geometry with a 35 mm×25 mm long neck, a conical section extending to 110 mm diameter at a plane 100 mm below the top, and a uniform cylindrical:flat bottomed vessel to a plane 270 mm below the top. Since a million or more cases were analyzed in order to obtain acceptable dose distributions, each involving tens of thousands of scattering events, one must be reasonable in accepting a simplified wall geometry for such surface dose calculations in such complex structures.

For interior wall dose calculations, we assumed a 10 micron thick annulus of dosimetry lining the bottle in order to replicate the FWT-810 film used in the measurements. This was divided into 8×2 cm vertical zones and 36 zones (i.e. 10°) around the azimuth. The wall dose calculations were referenced to an arbitrary 1000 kGy surface dose delivered at the neck entrance plane, first for the 36 azimuthal sectors, and then for the remaining 7×36 or 252 zones.

The dose distribution along the bottom surface was calculated on the assumption of a 10 micron dosimeter disk covering it, now divided into 3 radial zones with 36 (i.e. 10°) azimuthal subzones in each.

Figure 5:
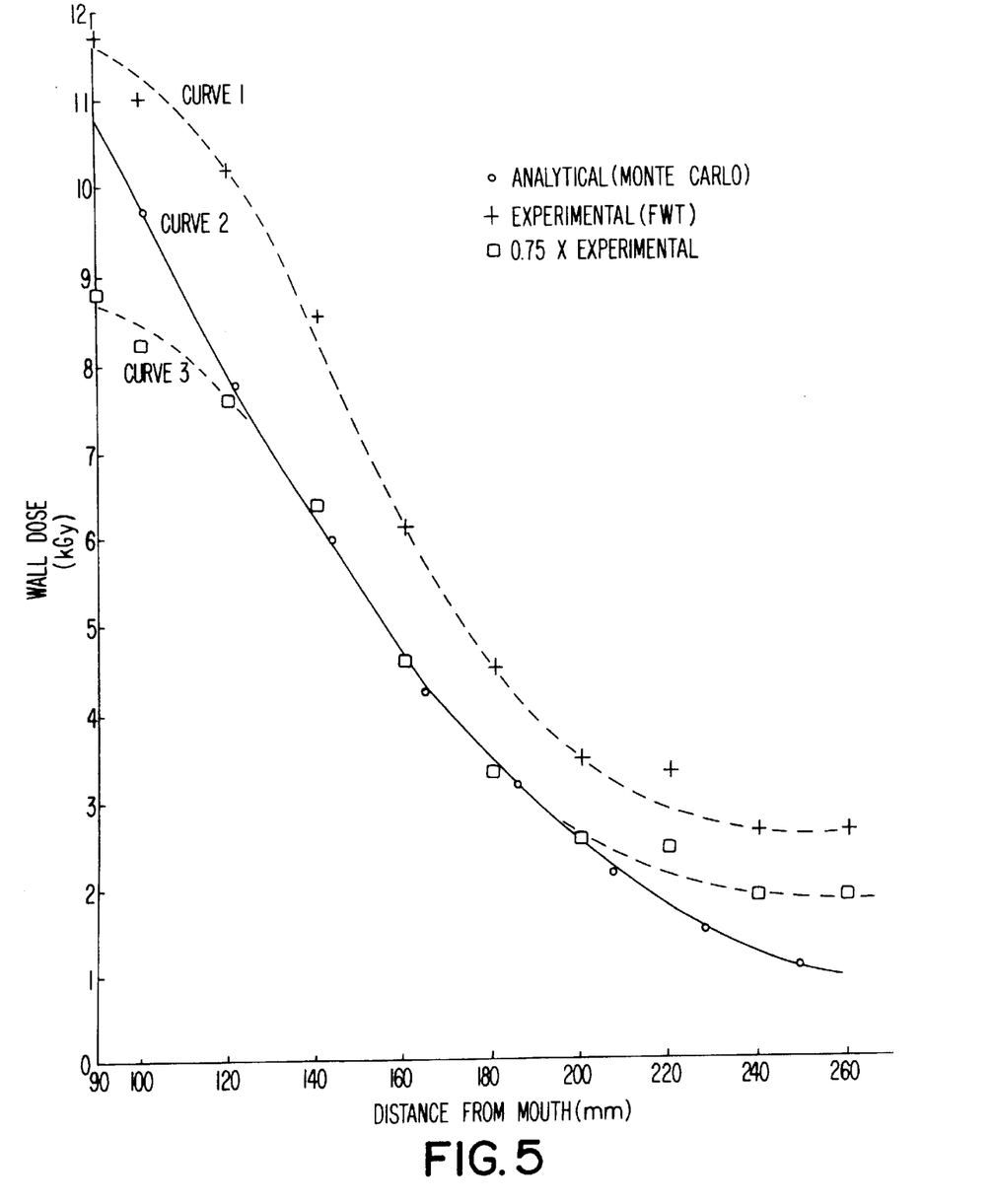
FIG. 5 is a graph showing certain dose distribution data.

FIG. 5 illustrates the level of agreement between the experimentally determined dose distribution for the lower cylindrical section of the bottle (90–260 mm from the mouth plane) and the Monte Carlo predictions.

Curve 1 shows these data for the bottle at an assumed surface dose of 2500 kGy. Curve 2 presents the results from the computer simulation referenced to a surface (mouth plane) dose of 1000 kGy. Curve 3 presents the experimental data normalized to 0.75 of the assumed 2500 kGy surface dose.

This figure shows the excellent agreement between the slopes of the dose fall-offs predicted and measured, except on the 90–120 mm zone where the bottle contour departs dramatically from the purely conical geometry assumed for the Monte Carlo model.

For the actual blow molded container, the wall bulges in at the 90 mm plane up to the base of the neck, and is not replicated well by the conical model. Hence the region beyond the 90 mm plane to the 120 mm level, is effectively "shielded" by the upper portions of the so-called conical section.

The model provides excellent insight into the internal electron dose distribution provided by such a confined geometry. The absolute difference between the experimental work and the model undoubtedly arises from the poor accuracy in experimental dose determination at the mouth opening plane. It is necessary to employ foil filtration techniques to desensitize the film at these very high dose levels, where optical density saturation can occur, and the resulting error in dose determination can be quite large.

Having thus described the principles of the invention, together with several illustrative embodiments thereof, it is to be understood that, although specific terms are employed, they are used in a generic and descriptive sense, and not for purposes of limitation, the scope of the invention being set forth in the following claims:

We claim:

1. Method of electron sterilizing, disinfecting or sanitizing an electron opaque open-mouthed container having an interior surface and an upper exterior surface, comprising the following steps:

producing a beam of electrons having an energy of the order of 100 keV, and conveying at least one open-mouthed container through said beam in an orientation such that said interior surface receives scattered electrons from said electron beam and sterlizes, sanitizes and/or disinfects said surface.

2. Method of electron sterilizing, disinfecting or sanitizing in accordance with claim 1, wherein, in conveying said at least one container through said beam, the upper exterior surface of said container is partially shielded so as to reduce the dose received thereby.

3. Method of electron sterilizing, disinfecting or sanitizing in accordance with claim 1, further comprising simultaneously delivering energetic electrons from the same source to the upper exterior surface of said container, and in doing so, controlling the external surface illumination.

4. Method according to claim 3, wherein said container is partially or completely filled with contents, thereby defining a head space between said contents and said open mouth, and wherein said electron sterilizing, disinfecting or sanitizing sanitizes or sterilizes said head space.

5. Method of curing electron polymerizable functional coatings applied or sprayed on the interior surfaces of a container, comprising the following steps:
producing a beam of electrons having an energy of the order of 100 keV, and
conveying at least one open-mouthed container through said beam in an orientation such that said interior surfaces receive scattered electrons from said electron beam and cures said coatings on said interior surfaces.

6. Method of curing electron polymerizable functional coatings according to claim 5, wherein said coatings are graftable functional coatings.

7. Apparatus for electron sterilizing an electron opaque open-mouthed container having an interior surface and an upper exterior surface, comprising in combination:
means for producing a beam of electrons having an energy of the order of 100 keV, and
means for conveying at least one open-mouthed container through said beam in an orientation such that said interior surface receives said electron beam.

8. Apparatus in accordance with claim 7, including means for partially shielding the upper exterior surface of said container so as to reduce the dose received thereby.

9. Apparatus according to claim 8, wherein said open mouth has a capping or sealing surface, and wherein said means for partially shielding includes an electron absorbing protective ring to prevent over dosage and thermal distortion of said capping or sealing surface of said open mouth of said container.

10. Apparatus according to claim 8, wherein said means for partially shielding includes a mask or ring which is spaced from the container opening to provide electron illumination of the external surface of the container.

11. Apparatus according to claim 8, wherein said means for partially shielding includes a mask having means for reducing electron albedo or backscatter which would affect the primary window of the sterilization.

12. Apparatus according to claim 8, wherein said means for partially shielding includes a mask which is positioned on a moving assembly so that the containers may be continuously positioned under the mask and removed from it after sterilization.

13. Apparatus according to claim 8, wherein said means for partially shielding includes a mask which is positioned on a moving assembly which will automatically shadow the container while in the electron treatment zone but which is then removed from return to the load point after sterilization for continuous processing.

14. Apparatus according to claim 8, wherein said means for partially shielding includes a mask which is positioned on an assembly which moves the container linearly along the beam and returns it to its starting location before removal, whereby a double longitudinal stroke results which will reduce the required length of the beam to accomplish the desired throughput.

15. Apparatus according to claim 8, wherein said means for partially shielding includes an electron stopping plate supported by a photon absorber, so that a collimated stream of bremsstrahlung results as the container and aperture pass along the beam.

16. Apparatus according to claim 7, wherein a fixed location real-time radiation monitor is provided to use said bremsstrahlung stream to verify the dose rate and beam energy delivered by the sterilizer to each container.

* * * * *